United States Patent [19]

Duncan et al.

[11] Patent Number: 4,508,116

[45] Date of Patent: Apr. 2, 1985

[54] CARBON DIOXIDE REBREATHING APPARATUS

[75] Inventors: David T. Duncan; David M. Lipscomb, both of Knoxville; John McElligott, Oliver Springs; Charles W. Williams, Powell, all of Tenn.

[73] Assignee: Products for Health and Industry, Knoxville, Tenn.

[21] Appl. No.: 454,036

[22] Filed: Dec. 28, 1982

[51] Int. Cl.$^3$ ............................................. A61M 16/00
[52] U.S. Cl. ........................... 128/203.28; 128/205.17; 128/914
[58] Field of Search ...................... 128/203.28, 205.11, 128/205.12, 205.13, 205.14, 205.17, 914, 207.14, 728; 272/99 R; 417/472, 473; 92/34, 92

[56] References Cited

U.S. PATENT DOCUMENTS

| 2,007,330 | 7/1935 | Hicks | 128/203.28 |
| 2,284,053 | 5/1942 | Hermann | 128/205.13 |
| 2,686,006 | 8/1954 | Hasselquist | 417/472 |
| 3,455,294 | 7/1969 | Adler et al. | 128/207.14 |
| 4,086,923 | 5/1978 | Henkin | 128/205.11 |
| 4,275,722 | 6/1981 | Sorensen | 128/200.24 |
| 4,301,810 | 11/1981 | Belman | 272/99 |

FOREIGN PATENT DOCUMENTS 389266 1/1924 Fed. Rep. of Germany ....................... 128/205.13

Primary Examiner—Henry J. Recla

Attorney, Agent, or Firm—Pitts and Brittian

[57] ABSTRACT

A rebreather apparatus for negating temporary hearing threshold shifts due to noise exposure and other physiological conditions related to $CO_2$ concentration. The rebreather is formed with three chambers. A mouthpiece communicates with a first chamber and this chamber has limited access to the second chamber sandwiched thereto. A third chamber is sandwiched to the second chamber and has limited communication with the second chamber. The third chamber has limited communication therefrom to the atmosphere thus providing an elongated air pathway from the atmosphere to the mouthpiece. This elongated pathway with the restrictions of the openings between chambers achieves an accumulation of carbon dioxide from a user's breath. Accordingly, air inhaled from the rebreather elevates the carbon dioxide content in the lungs of a user and thus in the blood stream of the user. This elevated carbon dioxide content has been shown to negate and/or prevent temporary hearing threshold shifts due to excessive noise exposure. In one embodiment the outer (third) chamber is collapsible during nonuse so that the rebreather may be carried in the pocket of the user and the second and third chambers have two portions symetrically positioned on opposite surfaces of the first chamber. In another embodiment at least the second and third chambers are collapsible. The device is made from inexpensive materials so that, if desired, it may be disposed of after use.

17 Claims, 8 Drawing Figures

CARBON DIOXIDE REBREATHING APPARATUS

DESCRIPTION

1. Technical Field

The present invention relates generally to apparatus for increasing the proportion of carbon dioxide in the air which a person breathes and more particularly to a rebreathing apparatus for achieving between about three percent (3%) and ten percent (10%) carbon dioxide in the air for the therapy of certain temporary hearing losses and uses for other conditions sensitive to the increased $CO_2$ concentration of inhaled air. It is intended to be used, for example, to provide a certain resistance to temporary hearing threshold shifts due to noise exposure, to overcome such temporary hearing threshold shifts, and to determine the difference between temporary and permanent hearing threshold shifts.

2. Background Art

Numerous developments have been made for applications in respiratory therapy. These are generally referred to as "rebreather" devices because a user's exhaled breath directed into some form of chamber is then reinhaled at least in part by the user. One such device is the Adler rebreather as manufactured by the Gaymar Industries, Inc., Buffalo, N.Y. This device is described, for example, in a publication entitled "Diseases of the Chest", Volume 2, Number 5, November, 1967. This device is generally cylindrical, is formed of a rigid plastic, and contains various internal baffles dividing the device into several chambers. The long air passages created by these baffles causes an accumulation of a portion of the carbon dioxide exhaled by a user. As this air is again reused within the body, the elevated level of carbon dioxide causes a stimulation whereby the breathing rate is increased which, among other results, produces a desirable breathing exercise which assists in post-operative recovery of the user.

Other devices within the class of rebreathers utilize an enclosure in which various medications are mixed with a user's exhaled air and upon further inhaling the medication is taken into the respiratory system. Typical of these devices are those shown in U.S. Pat. No. 1,044,367 issued Nov. 12, 1912 to G. A. Evans, U.S. Pat. No. 2,321,256 issued to F. L. Shelton on June 8, 1944 and U.S. Pat. No. 2,304,033 also issued to F. L. Shelton on Dec. 1, 1942. These devices, as well as the Adler rebreather, are intended for use with persons while they are substantially immobile, i.e. confined to a chair or a bed.

Recently it has been determined that a slight elevation in the carbon dioxide content of air inhaled by a person reverses temporary hearing threshold shifts due to noise exposure. As used herein, the term "temporary threshold shift" is defined as a reversable loss of hearing sensitivity. Furthermore, subjecting a person to this elevated carbon dioxide air often prevents or minimizes any temporary hearing threshold shifts due to the noise. If the temporary shift is not negated or prevented, permanent hearing damage can occur.

Accordingly, it is an object of the present invention to provide a device which may be used to increase the carbon dioxide content of air breathed by a user to overcome temporary hearing threshold shifts.

It is another object to provide a device which will permit an increase in the carbon dioxide level of the blood whereby a temporary hearing threshold shift due to noise exposure is prevented or reduced.

It is also an object of the present invention to provide a device for preventing or at least reducing temporary hearing threshold shifts due to noise, which device can be carried by a worker who anticipates or is subjected to noise exposure which otherwise may cause a temporary hearing threshold shift.

It is an additional object of the invention to provide a device for use in the prevention and/or stablization of physiological conditions sensitive to increased carbon dioxide concentration in inhaled air, such as pre- and post-operative hypoexpansion of the lungs, etc.

It is a further object of the present invention to provide a rebreather apparatus of sufficient rigid construction and yet disposable for use by industrial workers where undue noise may be present.

Other objects and advantages of the invention will become apparent upon a consideration of the detailed description and reference to the drawings.

DISCLOSURE OF THE INVENTION

The present invention is a rebreather apparatus of a size compatible with being carried by a worker who is often subjected to noise exposure that may produce a temporary hearing threshold shift. It is at least partially collapsible whereby the device will fit within a worker's pocket, and it is fabricated of materials which are inexpensive and therefore may be disposed of after periods of use. The device contains internal baffles having appropriate orifices whereby an extensive air flow path is achieved, with the volumes of the portions as defined by the baffles achieving an accumulation of from about three to ten percent (3%–10%) carbon dioxide when used by a worker.

BEST MODE FOR CARRYING OUT THE INVENTION

Figure 1:
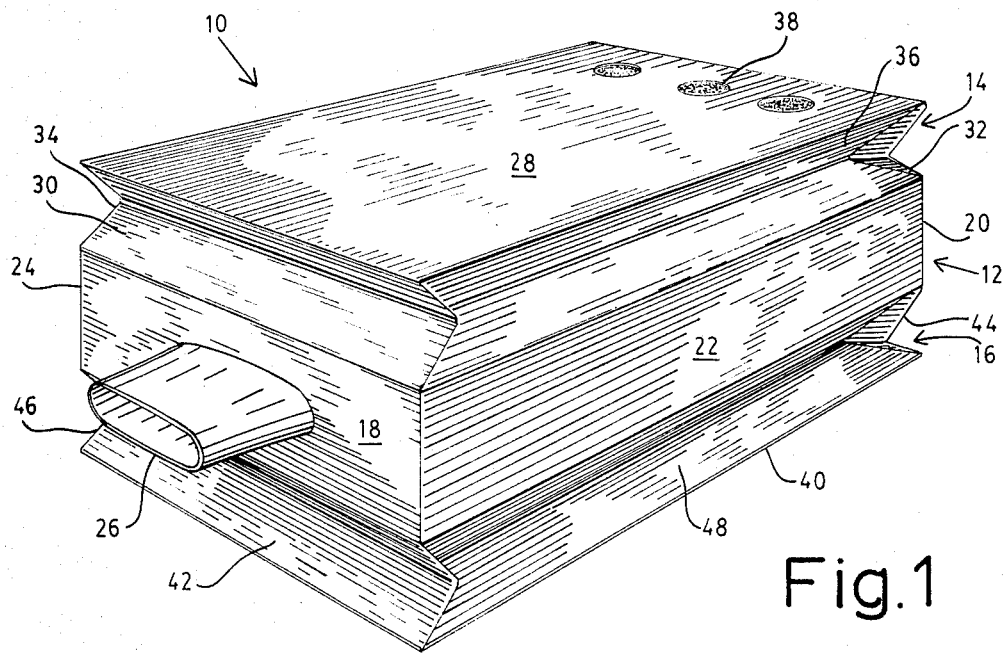
FIG. 1 is a perspective drawing of one embodiment of a rebreather according to the present invention.

Referring to FIG. 1, shown generally at 10 thereof is one embodiment of a rebreather according to the present invention. In this embodiment, there is a central non-collapsible portion 12 sandwiched between a pair of collapsible portions 14, 16. The non-collapsible portion 12 is formed with rigid end members 18, 20 as well as rigid side members 22, 24. It may be seen that a mouthpiece 26 is attached to end member 18. As will be discussed hereinafter, the mouthpiece 26 communicates with the interior of the rebreather. The upper collapsible portion 14 is formed with a rigid top panel 28 having its ends connected to ends 18, 20 with foldable end members 30, 32. Further, this collapsible portion 14 has a pair of foldable sides 34, 36 which attach the top panel 28 to the sides 22, 24. The top 28 is shown as being provided with three apertures 38 therethrough at an end opposite the mouth piece 26: other number of apertures providing the same resistance to air flow would be suitable.

The lower collapsible portion 16 is fabricated in a similar manner. A rigid bottom panel 40 is connected to ends 18, 20 with foldable portions 42, 44, and the foldable sides 46, 48 complete the collapsible portion 16. Although not shown, the panel 40 is also provided with apertures (e.g. three) therethrough in a position corresponding to the positions of apertures 38 in the top 28.

The rebreather shown in FIG. 1 is illustrated in the semi-collapsed (or semi-extended) condition. When fully extended, the ends 30, 32 of the portion 14, lie in the planes of the ends 18, 20, and the sides 34, 36 are substantially planar. The same is true for the lower collapsible portion 16. When fully collapsed the device is substantially no greater in thickness than the thickness of the non-collapsible portion 12.

Figure 2:
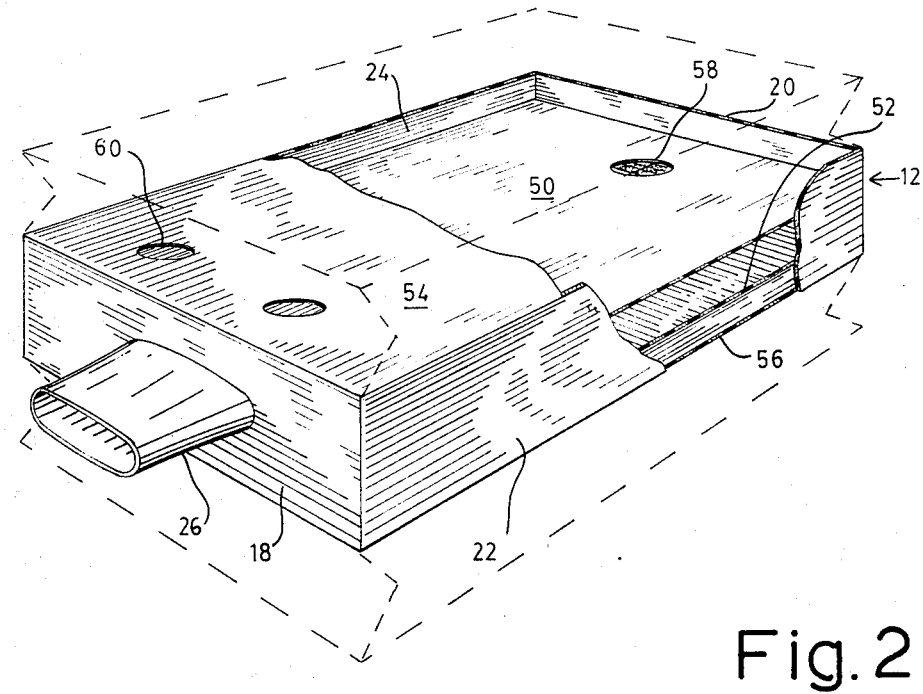
FIG. 2 is a perspective drawing, partially cut-away, showing the non-collapsible portion of the rebreather of FIG. 1.

The interior of the present invention is illustrated in FIG. 2 where the details of the non-collapsible portion 12 are shown. The interior is divided into several volumes by means of baffles. For example, a central volume is created between baffle 50 and baffle 52. It is into this volume that the afore-mentioned mouthpiece 26 communicates. A surrounding volume is created by baffles 54, 56 which are substantially parallel to the afore-mentioned baffles 50, 52. Each of these volumes utilizes the common edges 18, 20, 22 and 24, and communication therebetween is achieved with the opening 58 in baffle 50 near the end opposite the mouthpiece 26. A corresponding communication between the outer volume and the volume within the collapsible portions 14, 16 is achieved with a pair of apertures 60 or other numbers of apertures providing the same resistance to air flow. Although not shown, similar apertures are placed in baffle 56.

Figure 3:
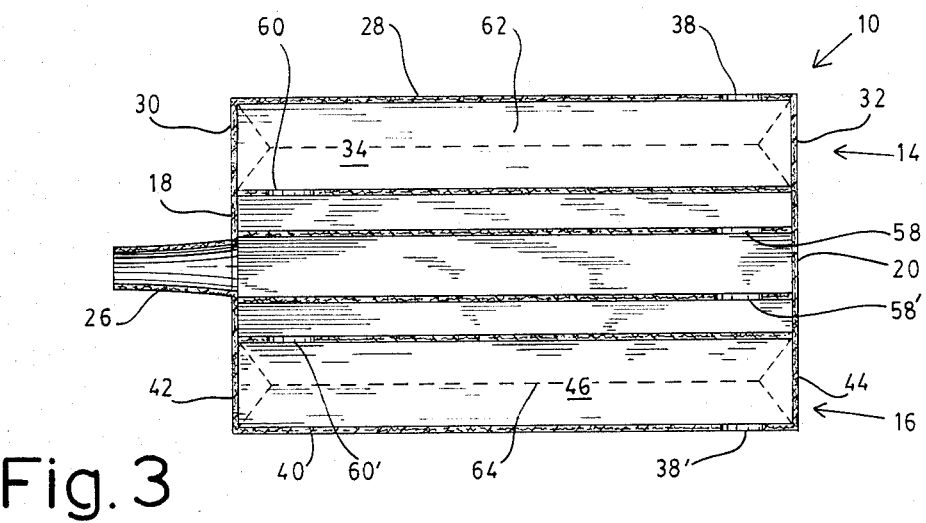
FIG. 3 is a longitudinal cross-section of the rebreather of FIG. 1.

A longitudinal cross-sectional view of the subject rebreather is illustrated in FIG. 3 where it is shown in a fully extended condition. In this drawing the various baffles which create the internal volumes are more clearly seen as well as the communication between the various volumes within the device. The dotted lines 62, 64 indicate the foldable side portions 34 and 46, respectively, of the collapsible portions 14, 16. The apertures in the various baffles which were not seen in FIGS. 1 and 2 are shown herein with the corresponding number primed (e.g. 38').

Figure 4:
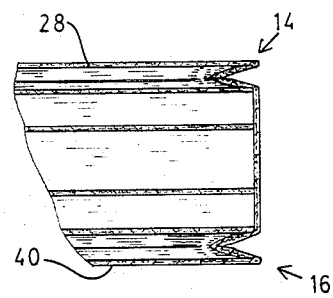
FIG. 4 is a partial longitudinal cross-sectional drawing illustrating the rebreather in a collapsed condition.

FIG. 4 illustrates a portion of the present rebreather, in cross-section, when the device is fully collapsed. It may be seen that the total thickness of the device assumes a thickness approximating that of the non-collapsible portion.

Figure 5:
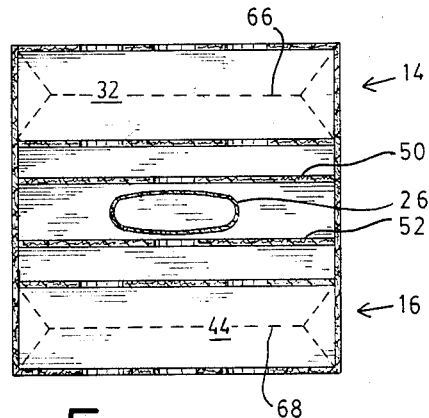
FIG. 5 is a transverse cross-section, taken at 5—5 of FIG. 3, of the rebreather shown in FIG. 1.

A transverse cross-section of the rebreather of FIGS. 1–4 is shown in FIG. 5. In this view it may be seen that the mouthpiece 26 enters the central volume between the baffles 50, 52. The dashed lines 66, 68 are used to indicate the foldable aspect of the ends 32, 44 respectively of the collapsible portions 14, 16.

Figure 6:
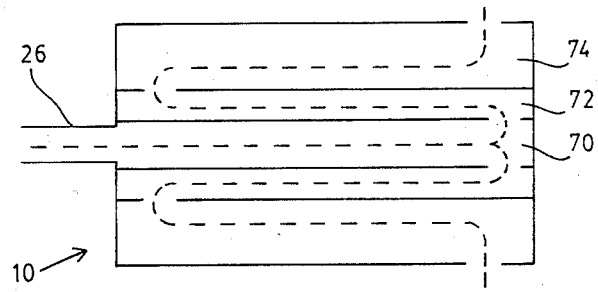
FIG. 6 is a schematic drawing illustrating the flow path of air through the rebreather of the subject design.

As discussed above, the present rebreather has a plurality of internal volumes with communication therebetween brought about by the apertures in the baffles that create these volumes. Accordingly, an extended flow path exists for air moving through the device. This extended flow path is illustrated in FIG. 6. It may be seen that exhaling flow exists through the mouthpiece 26 into the central volume 70. The flow is then out through apertures 58, 58' (see FIG. 3 for an identification of these specific apertures) into a surrounding volume 72. Further communication then exists through apertures 60, 60' into an outer volume 74 and then out through apertures 38, 38' to the atmosphere surrounding the device. Inhaling flow is in the reverse direction. The resistance to flow through the device causes a person using the same to rebreathe a portion of his or her exhaled air. Since the exhaled air has a carbon dioxide content greater than that of the atmosphere, the air taken into the lungs by a user increases in carbon dioxide content depending upon the resistance to flow. This increase in carbon dioxide can be maximized at from about three to about ten percent (3%–10%).

The exact level of carbon dioxide content with a reasonable length of use of the device is established by the relative size of the apertures in the various baffles. For example, a typical aperture size for the communication between the central volume 70 and the surrounding volume 72 is one centimeter. Using the same size aperture between the central volume 70 and the surrounding volume 72, although increasing the number of apertures by a factor of two, and using a aperture exiting to the atmosphere of 0.7 centimeters (with six such apertures), the carbon dioxide content of air within the device gradually builds to a level of approximately ten percent (10%). Increasing the size of the openings decreases the carbon dioxide content of air within the device, and reducing the size of the openings increases the percent of carbon dioxide. The aperture size can be chosen to achieve a desired result, i.e. a desired $CO_2$ content.

Figure 7:
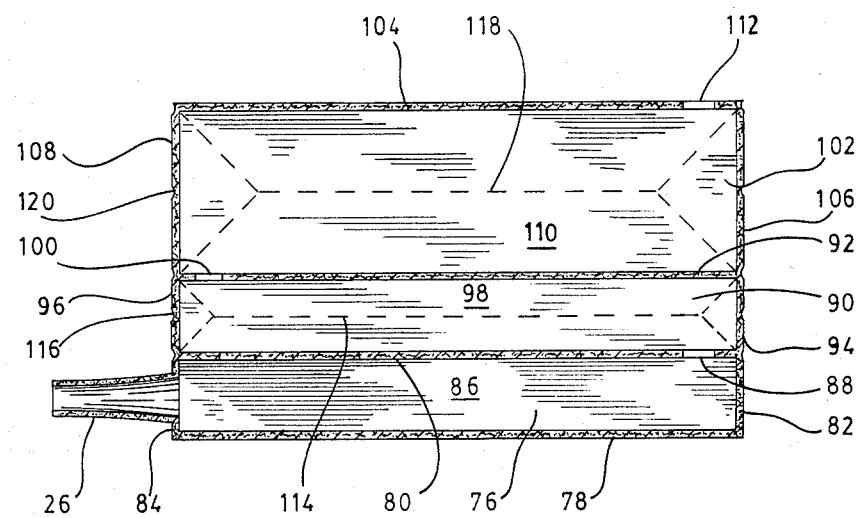
FIG. 7 is a longitudinal cross-section of another embodiment of the rebreather of the present invention.

Another embodiment of the present invention is illustrated in cross-section in FIG. 7. In this embodiment the mouthpiece 26 communicates with a breathing tube 76 which is equivalent to the chamber 70 shown in FIG. 6. The breathing tube 76 is constructed of a bottom plate 78, a top plate or baffle 80, end walls 82, 84 and a side plate 86. It will be understood that the second side plate is not visible in this drawing. The baffle 80 is provided with at least one aperture 88 at an end opposite that where the mouthpiece 26 is connected.

The aperture 88, corresponds to aperture 58 illustrated in FIG. 2, and communicates with an inner volume or chamber 90. The inner chamber 90 is defined by the aforementioned baffle 80, an upper baffle 92 parallel therewith, end walls 94, 96 and side wall 98. This inner chamber corresponds to the total volume of chamber 72 illustrated in FIG. 6. The baffle 92 is provided with one or more apertures 100 at the end near the mouthpiece 26. These apertures correspond to apertures 60 shown in FIG. 2 and communicate with a fresh air chamber 102. This chamber corresponds to the total volume within chamber 74 of FIG. 6.

The fresh air chamber 102 is formed by the aforementioned baffle 92, a top plate 104, end plates 106, 108 and a side panel 110. The top plate 104 is provided with at least one aperture 112 whereby the interior of the chamber 102 communicates with the atmosphere.

In the embodiment shown in FIG. 7, at least the inner chamber 90 and the fresh air chamber 102 are collapsible. This is indicated by the dashed line 114 for the inner chamber. This collapsing is accomplished, for example, by providing creased lines 116 or lines of reduced thickness in the end wall 96 and the other walls of the inner chamber. In a like manner, the fresh air chamber 102 may be collapsed as indicated by dashed line 118. This chamber is collapsed, for example, by folding the end wall 108 along a creased line 120 or a region of reduced thickness. It will be understood that the other walls of the chambers 90 and 102 are treated similarly to provide for the accordion-type collapsing of these chambers. Furthermore, if desired, the breathing tube 76 as well as the mouthpiece 26 may be formed to be collapsible in a similar fashion.

Figure 8:
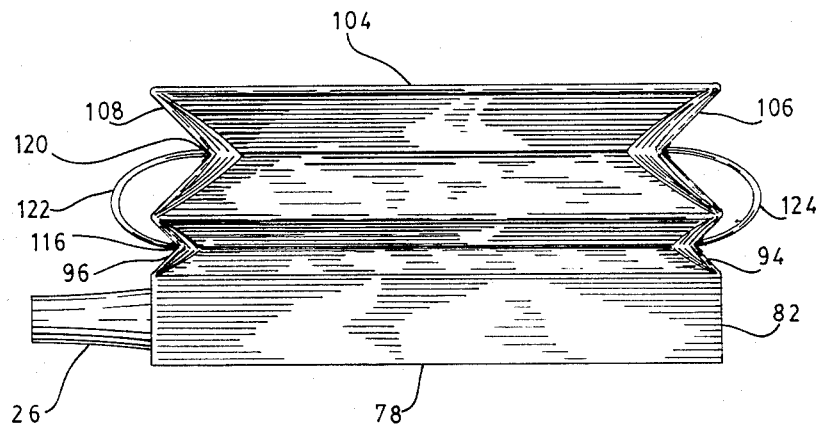
FIG. 8 is a side view of the rebreather embodiment of FIG. 7 when partially collapsed.

A side view of the embodiment of the rebreather of FIG. 7 is shown in FIG. 8. In this view the rebreather is shown as having a collapsible inner chamber and a collapsible fresh air chamber. In order that the collapsible sides may be drawn to their fully extended position as shown in FIG. 7, pull rings or tabs 122, 124 are provided. When a pulling action is applied to these tabs, the end walls 94, 96, 108 and 106 are extended to be coplanar with the end walls 82 and 84 of the breathing tube 76. It will be understood by those versed in the art that the side walls of the volumes are also drawn into a co-planar relationship with the side walls of the breathing tube.

It may be seen that having two of the compartments collapsible reduces the total thickness of the device, when in the collapsed position, to less than that of the embodiment shown in FIG. 1. Further reduction in thickness may be accomplished by forming the breathing tube such that it may also be collapsed.

The various volumes of the device are intended to be the same as those shown in the embodiment of FIG. 1. Furthermore, the cross-sectional area of the various apertures between the compartments are the same; thus, giving the same restriction to air flow as shown in the other embodiment. Accordingly, the rebreather of FIG. 7 provides for the same accumulation of carbon dioxide within the device and therefore the same level of carbon dioxide that is inhaled by a user of either embodiment.

As with the other embodiment, the embodiment shown in FIG. 7 may be fabricated from cardboard and paper or plastic components. Furthermore, since it may be desirable that a nose clamp be used by a person using the rebreather, this nose clamp may be utilized to hold the embodiment of FIG. 7 in a collapsed condition when not in use. This alternate embodiment provides for ease of construction. By one method, an outer box is fabricated with the mouthpiece inserted at its proper location, and the opposite end is provided with flaps. This box enclosing the inner chamber is then inserted into the outer box and appropriately glued at the end and along the edges. Subsequently, the flaps are closed and glued into place forming the finished product.

In another method of fabrication, a continuous strip is used. This strip is folded at appropriate locations to form essentially all of the surfaces of the various volumes. The edges are then applied to complete the structure. The components would be crimped prior to assembly to define the lines along which the sides and ends will fold to collapse the unit to its minimum size.

Research relative to the use of increased carbon dioxide partial pressures in the air inhaled by humans and certain animals is described in Archives of Otolaryngol, Volume 103, October 1977 and the American Journal of Otology, Volume 1, Number 4, April, 1980. These studies, which are incorporated by reference, were conducted using Carbogen (95% oxygen, 5% carbon dioxide). The "patients" were subjected to a test noise exposure which consisted of a ten minute duration, 100 decibel, 1000 Hertz pure tone signal. It was shown that with a ten minute treatment of the $CO_2$-containing gas, any temporary hearing shift was quickly negated by subsequent treatment. Also, the shift was substantially minimized by treatment with the gas prior to the imposition of the test signal.

The device described herein would be carried, for example, in a pocket of a worker. The worker would be instructed when assigned to an area of high levels of noise to periodically use the device for several minutes to increase the carbon dioxide content of the blood. This would substantially reduce any permanent effect of the high levels of noise upon the worker's hearing.

Because the device may be fabricated from inexpensive material, such as cardboard and paper or plastic, it may be disposed of following its use in the event that any type of contamination may exist in the region of the user. This would include use by persons in hospitals and the like where items in contact with the patient are often disposed of after the use by the patient.

From the foregoing description it will be recognized that an inexpensive rebreather apparatus is provided. It primarily can be used, for example, to negate the hearing shift of persons subjected to loud noises for prolonged periods of time. Also, if after use of the rebreather no recovery is noted, an indicator of possible permanent hearing damage is achieved. The device is useful for many physiological conditions sensitive to increased $CO_2$ concentration in inhaled air. These conditions include rapid respiratory rate, pre-and post-operative hypoextension of the lungs and vasodilation of blood vessels in acute stroke victims. It also is beneficial in increasing the tidal volume in patients with poor pulmonary reserve. It is readily manufactured of low cost materials so that it can be disposed of, if desired, after its use.

It is, of course, understood that although a preferred embodiment of the present invention has been illustrated and described, various modifications thereof will become apparent to those skilled in the art. Accordingly, the scope of the invention should be defined only by the appended claims and the equivalence thereof.

We claim:

1. A rebreathing device for increasing the carbon dioxide concentration of air inhaled by a user, which comprises:
    a first rectangular prism-shaped chamber of a selected volume defined by planar non-collapsible enclosure walls, and having side walls adjoined to a first end wall and a further end wall, and provided with a mouthpiece communicating therewith at said first end wall;
    a second rectangular prism-shaped chamber, having a selected volume relative to said volume of said first chamber, defined by planar enclosure walls including side walls adjoined to a first and a further end wall and a common side wall with said first chamber, said common wall being provided with opening means adjacent said further end walls of said first and second chambers communicating between said first and second chambers;
    a third rectangular prism-shaped chamber adapted for collapse when said device is not in use, having a selected volume relative to said first and second chambers, defined by planar collapsible and non-collapsible walls including collapsible opposed side walls adjoined to first and further collapsible end walls, and a common non-collapsible side wall with said second chamber and a non-collapsible wall opposed to said common wall, said common wall being provided with opening means adjacent said first end walls of said second and third chambers communicating between said second and third chambers, and said opposed non-collapsible wall being provided with opening means communicating with the atmosphere surrounding said device; whereby said first, second and third chambers, and said openings communicating between said chambers, produce an extended restricted flow path along the additive lengths of said first, second and third chambers between said mouthpiece and said opening to the atmosphere thereby producing an accumulation of breath of a user with a corresponding accumulation of carbon dioxide in the device and in air inhaled by said user.

2. The device of claim 1 wherein the length and width of each of the chambers is equal, the length is greater than the width, and the width is greater than the thickness of each.

3. The device of claim 2 wherein end and side wall portions of said enclosure walls of said second chamber are provided with accordion-type folds whereby said second chamber is adapted for collapse when said device is not in use.

4. The device of claim 2 wherein end and side wall portions of said enclosure walls of said second and said third chambers are provided with accordion-type folds whereby said first and said second chambers are adapted for collapse when said device is not in use.

5. The device of claim 2 wherein said width and length of said first, second and third chambers are about 8 centimeters and 12 centimeters, respectively; said thickness of said first chamber is about 1 centimeter, said thickness of said second chamber is about 1.5 centimeters; said thickness of said third chamber is about 5 centimeters; and said thickness of said device is about 7.5 centimeters.

6. The device of claim 2 wherein said second chamber is divided into two substantially equal first and second portions with said first and said second portions sandwiched on either side of said first chamber and adjoined thereto by common side walls wherein said first and second portions are provided in said common side walls adjacent said first end wall with said opening means of selected size communicating with said first chamber at a position adjacent said further end wall of said first chamber.

7. The device of claim 6 wherein said third chamber is divided into two substantially equal first and second portions with said first and second portions sandwiched on either side of said second chamber and adjoined thereto by common side walls wherein said first and second portions of said third chamber are provided in said common side walls adjacent said first end wall with said opening means of selected size communicating with said second chamber at a position adjacent said further end wall of said second chamber, said side walls of said third chamber opposite said common side walls provided with said opening means communicating said third chamber to the atmosphere.

8. The device of claim 7 wherein ends and sides of said first portion of said third chamber are provided with accordian-type folds, thereby permitting the top surface thereof to be collapsed toward said first portion of said second chamber and wherein ends and sides of said second portion of said third chamber are provided with accordion-type folds thereby permitting a bottom surface thereof to be collapsed toward said second portion of said second chamber.

9. The device of claim 8 wherein said ends and sides of said first and said second portions of said third chamber fold inwardly whereby said top surface and said bottom surface collapse perpendicularly with respect to said first and said second portions of said second chamber.

10. The device of claim 7 wherein the length and width of said first, second and third chambers are about 12 centimeters and 8 centimeters, respectively; the thickness of said first chamber is about 1 centimeter; the thickness of each of said first and said second portions of said second chamber is about 0.75 centimeters; and the thickness of each of said first and second portions of said third chamber is about 2.5 centimeters.

11. The device of claim 10 wherein said opening means between said first chamber and said second chamber is a pair of single circular holes of about 1 centimeter in diameter, one communicating with said first portion of said second chamber and the other communicating with said second portion of said second chamber; wherein said opening means between said second chamber and said third chamber is two pairs of two circular holes, each of about 1 centimeter in diameter, with one pair communicating between said first portion of said second chamber and said first portion of said third chamber and the other pair communicating between said second portion of said second chamber and said second portion of said third chamber; and wherein said opening means between said third chamber and the atmosphere is two groups of three circular holes, each about 0.7 centimeters in diameter, with one group communicating between said first portion of said third chamber and the atmosphere and the other group communicating between said second portion of said third chamber and the atmosphere.

12. The device of claim 1 wherein said first chamber has a volume of about 96 cubic centimeters; said second chamber has a volume of about 144 cubic centimeters; said third chamber has a volume of about 480 cubic centimeters; said opening between said first chamber and said second chamber has an area of about 1.77 square centimeters; said opening between said second chamber and said third chamber has an area of about 3.14 square centimeters; said opening between said third chamber and the atmosphere has an area of about 2.3 square centimeters; and said device increases said carbon dioxide concentration to about ten percent (10%) during use by a user.

13. A rebreathing device to be used by a person for increasing the carbon dioxide concentration of air inhaled by said person which comprises:
a rigid elongated rectangular prism first chamber having a length, width and thickness to define a first selected volume;
a rigid elongated rectangular prism second chamber having a length and width equal to said length and width of said first chamber and having a total thickness to define a second selected volume, said second chamber divided into two substantially equal first and second portions sandwiched on either side of said first chamber with a common first partition between said first portion of said second chamber and said first chamber and a second common partition between said second portion of said second chamber and said first chamber;

a collapsible elongated substantially rectangular prism third chamber having a length and width equal to said length and width of said first chamber and having a total thickness to define a third selected volume, said third chamber divided into two substantially equal first and second portions sandwiched on either side of said device with a first common partition between said first portion of said third chamber and said first portion of said second chamber and a second common partition between said second portion of said second chamber and said second portion of said third chamber;

a mouthpiece for said user communicating with a first end of said first chamber;

wherein said common partitions between said first chamber and said first and second portions of said second chamber are each provided with a single opening therein near a further end of said first chamber;

wherein said common partitions between said first and second portions of said second chamber and said first and second portions of said third chamber are each provided with a pair of openings therein near an end oriented toward said mouthpiece; and wherein said first and said second portions of said third chamber are each provided with three openings therein near an end opposite said mouthpiece, which openings communicate with the atmosphere thereby producing an extended continuous air path from the atmosphere about the device to the mouth of a user at said mouthpiece, which air path is restricted by said openings between chambers to produce an accumulation of carbon dioxide from a user's breath within said device and thereby enchance the carbon dioxide content of air inhaled by said person from said device.

14. A rebreathing device to be used by a person for increasing the carbon dioxide concentration of air inhaled by said person which comprises:

an elongated rectangular prism first chamber having a length, width and thickness to define a first selected volume;

a collapsible elongated rectangular prism second chamber having a length and width equal to said length and width of said first chamber and having a thickness to define a second selected volume, greater than the volume of said first chamber said second chamber sandwiched upon said first chamber with a common first partition between said second chamber and said first chamber, said first partition having a length and width substantially equal to said length and width of said first chamber;

a collapsible elongated rectangular prism third chamber having a length and width equal to said length and width of said first chamber and having a thickness to define a third selected volume greater than the volume of said second chamber, said third chamber sandwiched upon said second chamber with a second common partition between said third chamber and said second chamber, said second partition having a length and width substantially equal to said length and width of said first chamber;

a mouthpiece for said user communicating with a first end of said first chamber;

wherein said common partitions between said first chamber and said first and second portions of said second chamber are each provided with a single opening therein near a further end of said first chamber;

wherein said common partitions between said first and second portions of said second chamber and said first and second portions of said third chamber are each provided with a pair of openings therein near an end oriented toward said mouthpiece; and wherein said first and said second portions of said third chamber are each provided with three openings therein near an end opposite said mouthpiece, which openings communicate with the atmosphere thereby producing an extended continuous air path from the atmosphere about the device to the mouth of a user at said mouthpiece, which air path is restricted by said openings between chambers to produce an accumulation of carbon dioxide from a user's breath within said device and thereby enchance the carbon dioxide content of air inhaled by said person from said device;

a mouthpiece for said user communicating with a first end of said first chamber;

wherein said first partition between said first chamber and said second chamber is provided with a first opening therein near a further end of said first chamber;

wherein said second partition between said second chamber and said third chamber is each provided with a second opening therein near an end oriented toward said mouthpiece; and wherein said third chamber is provided with a third opening therein near an end opposite of said mouthpiece, which third opening communicates with the atmosphere thereby producing an extended continuous air path from the atmosphere about the device to the mouth of a user at said mouthpiece, which air path is restricted by said openings between chambers to produce an accumulation of carbon dioxide from a user's breath within said device and thereby enchance the carbon dioxide content of air inhaled by said person from said device.

15. The device of claim 14 wherein said volume of said first chamber is about 96 cubic centimeters; said volume of said second chamber is about 144 cubic centimeters; said volume of said third chamber is about 480 cubic centimeters; said first opening is circular with a diameter of about 1.5 centimeters; said second opening is four circular perforations each of about 1 centimeter in diameter; and said third opening is six perforations each of about 0.7 centimeters in diameter.

16. The device of claim 15 wherein the width and length of said first, second and third chambers are about 8 centimeters and 12 centimeters respectively, and said device produces an accumulation of about 10% carbon dioxide in air inhaled by said user.

17. A rebreathing device for increasing the carbon dioxide concentration of air inhaled by a user, which comprises:

a first rectangular prism-shaped chamber having a selected volume defined by enclosure walls, and having a first end and a further end, and provided with a mouthpiece communicating therewith at said first end;

a second rectangular prism-shaped chamber having a selected volume, relative to said volume of said first chamber, defined by enclosure walls and having a first end and a further end, said second chamber provided at said first end with opening means of a selected size communicating with said further end of said first chamber, and wherein said second chamber is divided into two substantially equal first and second portions with said first and said second portions sandwiched on either side of said first chamber with said opening means between said first chamber and said second chamber communicating with both said first and said second portions of said second chamber;

a third rectangular prism-shaped chamber having a selected volume, relative to volumes of said first and second chambers, defined at least in part by collapsible walls and having a first end and a further end, said third chamber provided at said first end with first opening means of a selected size communicating with said further end of said second chamber and provided at said further end with second opening means of a selected size communicating with the atmosphere surrounding said device and wherein said third chamber is divided into two substantially equal first and second portions with said first and said second portions sandwiched on either side of said second chamber with said first opening means between said second chamber and said third chamber communicating with both said first and second portions of said third chamber;

wherein the length and width of each of the chambers is equal, the length is greater than the width, and the width is greater than the thickness of each; and whereby said first, second and third chambers, and said openings communicating between said chambers, produce an extended restricted flow path between said mouthpiece and said opening to the atmosphere thereby producing an accumulation of breath of a user with a corresponding accumulation of carbon dioxide in the device and in air inhaled by said user.

* * * * *